United States Patent [19]
Yamaura

[11] Patent Number: 6,019,723
[45] Date of Patent: Feb. 1, 2000

[54] ULTRASONIC DIAGNOSTIC APPARATUS, CURSOR DISPLAY METHOD AND MEASURING APPARATUS

[75] Inventor: Koichi Yamaura, Tokyo, Japan

[73] Assignee: GE Yokogawa Medical Systems, Limited, Tokyo, Japan

[21] Appl. No.: 09/169,301

[22] Filed: Oct. 8, 1998

[30] Foreign Application Priority Data

Nov. 17, 1997 [JP] Japan .................................. 9-315186

[51] Int. Cl.$^7$ ........................................................ A61B 8/00
[52] U.S. Cl. ........................ 600/437; 600/441; 600/443; 345/418
[58] Field of Search ..................................... 600/449, 443, 600/447, 437, 441; 345/1, 163, 443

[56] References Cited

U.S. PATENT DOCUMENTS 5,588,435  12/1996  Wong et al. .
5,605,155   2/1997  Chalana et al. .
5,682,896  11/1997  Scheib et al. .
5,724,973   3/1998  Spratt .

FOREIGN PATENT DOCUMENTS 0617921  10/1994  European Pat. Off. .

Primary Examiner—Francis J. Jaworski
Assistant Examiner—Ali M. Imam
Attorney, Agent, or Firm—Moonray Kojima

[57] ABSTRACT

In order to decrease the amount of operation required for an operator to move a cursor and in order to allow the operator to distinctly view deviation of CRL (Crown Rump Length) of a fetus from a normal value, when an ultrasonic image of a fetus F is displayed and a first cursor C1 is positioned at the head (or the rump) of the fetus F, a second cursor C2 is initially displayed at a position which corresponds to a normal CRL obtained from GA (Gestation Age) estimated from the last menstruation date. When the second cursor C2 is moved and positioned at the rump (or the head) of the fetus F, the measured CRL and GA estimated therefrom are displayed.

3 Claims, 5 Drawing Sheets

FIG. 4A

61  Cursor position determination table

| Measured item | 1st cursor position | 2nd cursor position | Action |
|---|---|---|---|
| | X, Y | + x, +y | |
| TOKYO CRL | 300, 200 | + 0, + f (GA) | ON |
| TOKYO DPD | 200, 200 | 400, 300 | ON |
| XXXXX | 100, 200 | q (GA), 100 | OFF |
| | | | |

FIG. 4B

Separate table

| f ( GA ) ( TOKYO CRL) | GA |
|---|---|
| | |
| | |
| + 20 mm | 62 |
| + 21 mm | 63 |
| + 22 mm | 64 |
| | |
| | |

ULTRASONIC DIAGNOSTIC APPARATUS, CURSOR DISPLAY METHOD AND MEASURING APPARATUS

BACKGROUND OF THE INVENTION

The present invention relates to an ultrasonic diagnostic apparatus, a cursor display method and a measuring apparatus which can decrease the amount of operation required for an operator to move a cursor and allow the operator to distinctly view deviation of a first attributive value of an object from a normal value.

The process for CRL (Crown Rump Length) measurement by a conventional ultrasonic diagnostic apparatus will be described hereinafter.

As shown in FIG. 1(a), an image of a fetus F taken by an ultrasonic probe is displayed on a screen.

As shown in FIG. 1(b), a first cursor C1 is initially displayed in an initial position at the center of the screen.

As shown in FIG. 1(c), the operator moves the first cursor C1 and positions it at the head (or the rump) of the fetus F.

As shown in FIG. 1(d), a second cursor C2 is initially displayed in an initial position located 10 mm straight below the first cursor C1.

As shown in FIG. 1(e), the operator moves the second cursor C2 and positions it at the rump (or the head) of the fetus F.

Then, as shown in FIG. 1(f), the distance between the first cursor C1 and the second cursor C2 is converted into an actual length and the length is displayed as the CRL on the screen. (In this example, CRL=20 mm.) Also, GA (Gestation Age) which is estimated from the measured CRL based on normal correlation between GA and CRL is displayed on the screen. (In this example, GA=62 days.) Growth is determined by numerically comparing the GA estimated from the last menstruation date (e.g., 63 days) with the GA estimated from the CRL (e.g., 62 days). In addition, growth is also determined from a graph as shown in FIG. 2.

However, there are the following problems in using the conventional ultrasonic diagnostic apparatus:
(1) Since the initial positions of the first and second cursors are fixed, the amount of operation required for moving the cursor often increases when the cursor is positioned at the image of an object; and
(2) Without a graph, deviation of the first attributive value of the object from a normal value can not be distinctly ascertained.

SUMMARY OF THE INVENTION

It is the object of the present invention to provide an ultrasonic diagnostic apparatus, a cursor display method and a measuring apparatus which decrease the amount of operation required for an operator to move a cursor and allow the operator to distinctly view deviation of a first attributive value of an object from a normal value.

In accordance with a first aspect, the present invention provides an ultrasonic diagnostic apparatus comprising: image display means for displaying on a screen an image of an object taken by an ultrasonic probe; first cursor initial display means for initially displaying a first cursor on the screen; first cursor positioning means for moving the first cursor and positioning it in response to an operation by an operator; second cursor initial display means which finds a normal value with respect to an on-screen positional relationship between the first cursor and a second cursor from normal correlation between first and second attributive values of the object, then finds an initial position for the second cursor based on the normal value and the position of the first cursor, and initially displays the second cursor at the initial position on the screen; second cursor positioning means for moving the second cursor and positioning it in response to an operation by the operator; and measuring means for measuring the first attributive value of the object using an on-screen positional relationship between the first and second cursors.

In the ultrasonic diagnostic apparatus according to the first aspect, the second cursor is initially displayed not at a fixed position but an initial position determined by finding a normal first attributive value from a known second attributive value using normal correlation between the second and first attributive values, and then finding the initial position for the second cursor based on the normal first attributive value and the position of the first cursor. Thus, deviation of the initial display position of the second cursor from the image of the object is reduced, and hence, the amount of operation required for the operator to move the second cursor can be decreased. Moreover, deviation of the initial display position of the second cursor from the image of the object represents deviation of the first attributive value of the object from a normal value, thus allowing the operator to distinctly view deviation of the object from normal.

In accordance with a second aspect, the present invention provides the ultrasonic diagnostic apparatus as described regarding the first aspect, wherein the first cursor initial display means can change the initial position at which the first cursor is initially displayed according to the class of the first attributive value.

In the ultrasonic diagnostic apparatus according to the second aspect, the first cursor is initially displayed at an initial position according to the class of the first attributive value, instead of at a fixed position. Thus, deviation of the initial display position of the first cursor from the image of the object is reduced, and hence, the amount of operation required for the operator to move the first cursor can be decreased.

In accordance with a third aspect, the present invention provides the ultrasonic diagnostic apparatus as described regarding the first and second aspects, wherein the object is a fetus, the class of the first attributive value is CRL (Crown Rump Length), and the class of the second attributive value is GA (Gestation Age).

In the ultrasonic diagnostic apparatus according to the third aspect, the second cursor is initially displayed not at a fixed position but an initial position determined by finding a normal CRL from a known GA (estimated from the last menstruation date) using normal correlation between GA and CRL, and then finding the initial position for the second cursor based on the normal CRL and the position of the first cursor. Thus, deviation of the initial display position of the second cursor from the image of the fetus is reduced, and hence, the amount of operation required for the operator to move the second cursor can be decreased. Moreover, deviation of the initial display position of the second cursor from the image of the fetus represents deviation of CRL of the fetus from a normal value, thus allowing the operator to distinctly view whether the growth of the fetus is advancing or retarded.

In accordance with a fourth aspect, the present invention provides a cursor display method comprising the steps of: displaying an image of an object on a screen; positioning a first cursor at the image; finding an initial position for a second cursor and initially displaying the second cursor at the initial position, the initial position being found based on a normal value with respect to an on-screen positional relationship between the first and second cursors, as well as on the position of the first cursor, the normal value being found from normal correlation between first and second attributive values of the object; positioning the second cursor at the image; and measuring the first attributive value of the object by an on-screen positional relationship between the first and second cursors.

In the cursor display method according to the fourth aspect, the second cursor is initially displayed not at a fixed position but an initial position determined by finding a normal first attributive value from a known second attributive value using normal correlation between the second and first attributive values, and then finding the initial position for the second cursor based on the normal first attributive value and the position of the first cursor. Thus, deviation of the initial display position for the second cursor from the image of the object is reduced, and hence, the amount of operation required for the operator to move the second cursor can be decreased. Moreover, deviation of the initial display position of the second cursor from the image of the object represents deviation of the first attributive value of the object from a normal value, thus allowing the operator to distinctly view deviation of the object from normal.

In accordance with a fifth aspect, the present invention provides a measuring apparatus comprising: image display means for displaying on a screen an image of an object; first cursor initial display means for initially displaying a first cursor on the screen; first cursor positioning means for moving the first cursor and positioning it in response to an operation by an operator; second cursor initial display means which finds a normal value with respect to an on-screen positional relationship between the first cursor and a second cursor from normal correlation between first and second attributive values of the object, then finds an initial position for the second cursor based on the normal value and the position of the first cursor, and initially displays the second cursor at the initial position on the screen; second cursor positioning means for moving the second cursor and positioning it in response to an operation by the operator; and measuring means for measuring the first attributive value of the object by an on-screen positional relationship between the first and second cursors.

In the measuring apparatus according to the fifth aspect, the cursor display method as described regarding the fourth aspect is suitably implemented, and therefore the amount of operation required for the operator to move the second cursor can be decreased. Moreover, the operator can distinctly view deviation of the object from normal.

Further objects and advantages of the present invention will be apparent from the following description of the preferred embodiments of the invention as illustrated in the accompanying drawings.

BRIEF DESCRIPTION OF THE DRAWINGS

FIG. 4 is a configuration diagram of a cursor position determination table.

DETAILED DESCRIPTION OF THE INVENTION

The present invention will now be described in more detail with reference to an embodiment shown in the accompanying drawings.

Figure 1A:
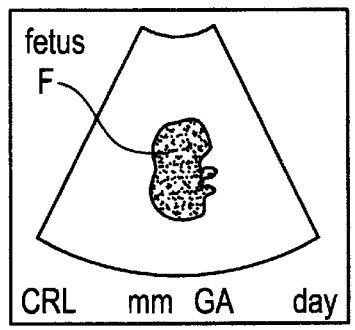
FIG. 1 is an explanatory diagram illustrating one example of the conventional cursor display.
Figure 1B:
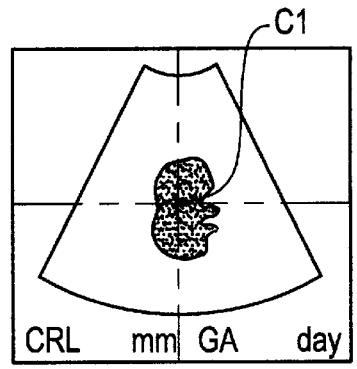
Figure 1C:
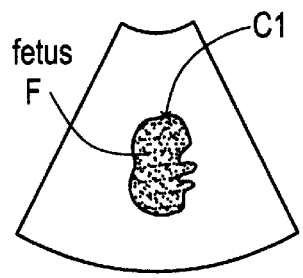
Figure 1D:
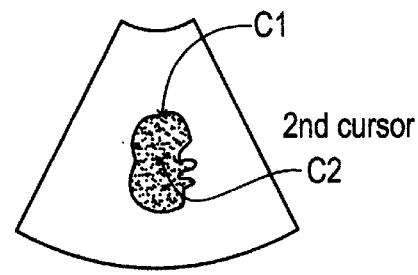
Figure 1E:
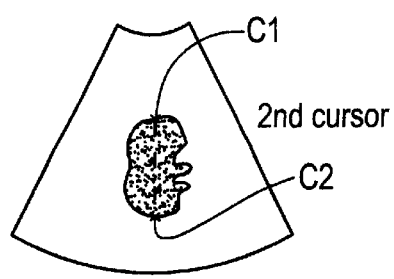
Figure 1F:
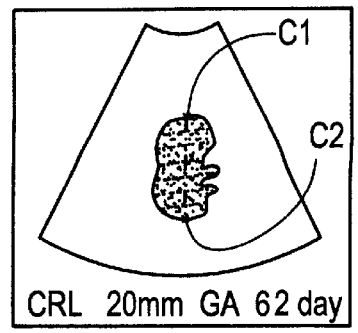
Figure 2:
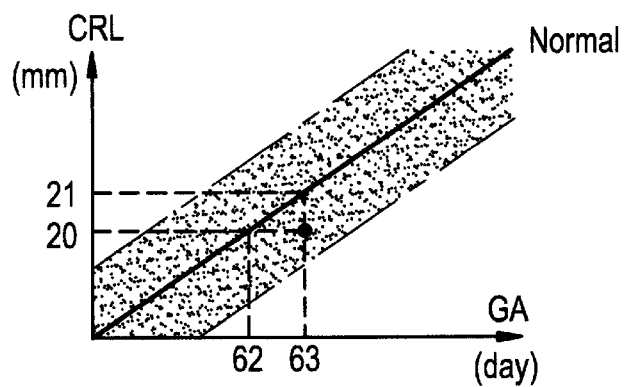
FIG. 2 shows an example of a graph which is conventionally used to ascertain growth of a fetus.
Figure 3:
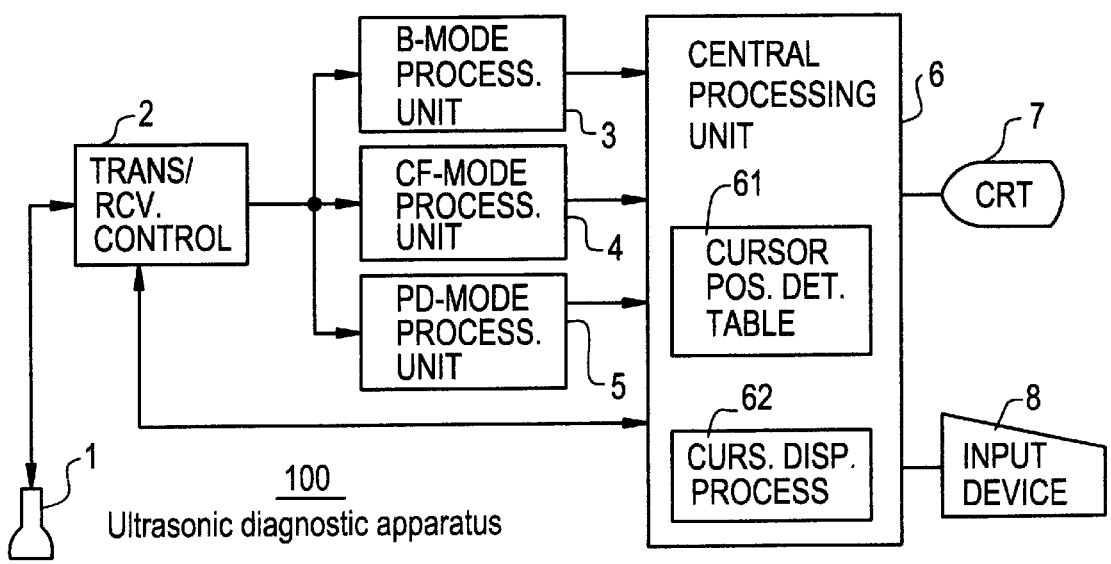
FIG. 3 is a block diagram illustrating an ultrasonic diagnostic apparatus in accordance with one embodiment of the present invention.

FIG. 3 is a block diagram illustrating an ultrasonic diagnostic apparatus in accordance with one embodiment of the present invention.

The ultrasonic diagnostic apparatus 100 comprises an ultrasonic probe 1 for transmitting ultrasonic pulses and receiving an ultrasonic echo, a transmit/receive controller 2 for electronically scanning a scanning plane to acquire sound-ray signals, a B-mode processing unit 3 for generating image data based on the intensity of the ultrasonic echo, a CF-mode processing unit 4 for generating image data based on the phase of the Doppler component of the ultrasonic echo, a PD-mode processing unit 5 for generating image data based on the power of the Doppler component of the ultrasonic echo, a central processing unit 6 for producing a display image from the image data, a CRT (cathode-ray tube) 7 for presenting the display image, and an input device 8 which allows the operator to input commands.

The central processing unit 6 comprises a cursor position determination table 61 and a cursor display processing routine 62.

FIG. 4(a) is a configuration diagram of the cursor position determination table 61.

In the cursor position determination table 61 are included: "First cursor position" in which the initial position for the first cursor (in the screen x-y coordinate) is registered, "Second cursor position" in which the initial position for the second cursor (in the screen x-y coordinate) is registered, and "Action" in which the value "ON" or "OFF" is registered to respectively indicate whether or not the cursor positions specified in the cursor position determination table 61 are to be used. "First cursor position", "Second cursor position" and "Action" are specified for every measured item.

In "First cursor position" and "Second cursor position" described above, an unsigned value (e.g., 300) or an unsigned function represents the coordinate value, and a signed value (e.g., +0) or a signed function (e.g., +f(GA)) represents the relative coordinate value with reference to another cursor position which has been determined. The function is defined in a separate table.

FIG. 4(b) is a configuration diagram of one example of the separate table.

The separate table defines values of GA and f(GA), and the value of f(GA) is a normal CRL value for a GA value.

Figure 5:
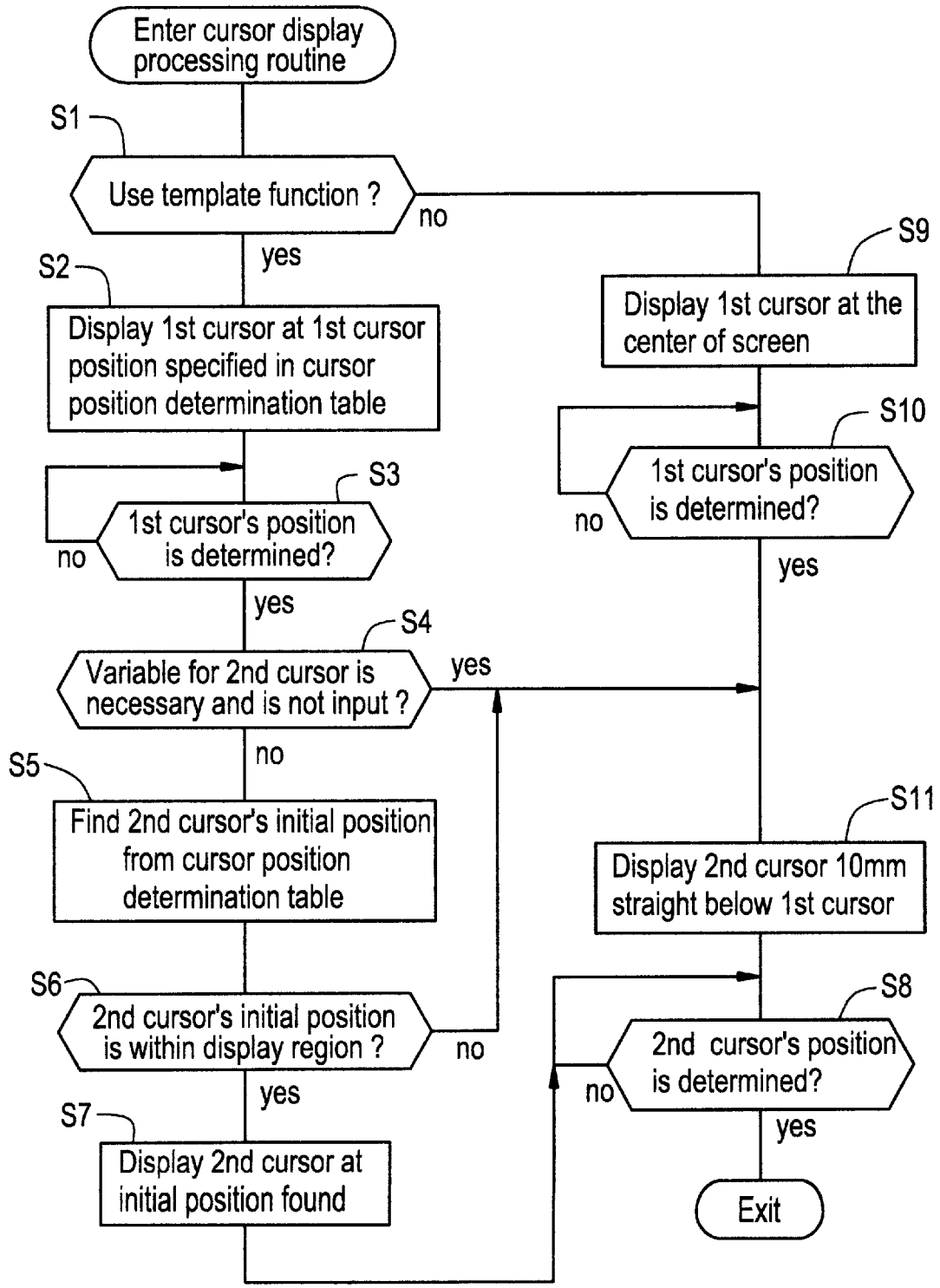
FIG. 5 is a flow chart of the cursor display processing routine.

FIG. 5 is a flow chart of the cursor display processing routine 62.

Figure 6A:
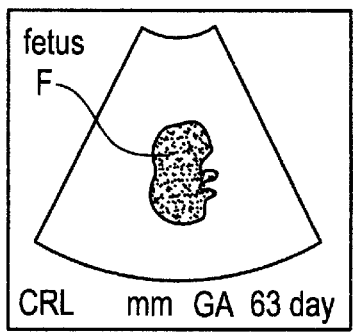
FIG. 6 is an explanatory view of cursor display in accordance with one embodiment of the present invention.

The cursor display processing routine 62 is activated when an image of a fetus F taken by the ultrasonic probe is displayed on the screen and the measuring operation is started, as shown in FIG. 6(a). In this example, the measured item is assumed to be CRL, and GA estimated from the last menstruation date is assumed to be input as patient information. In this case, the measured item name, "CRL", and the GA value (e.g., GA=63 days) are displayed on the screen.

In Step S1, the cursor position determination table 61 is retrieved using the current measured item as a retrieval key.

If "Action" for the corresponding record is "ON", the process goes to Step S2; and if "Action" is "OFF", the process goes to Step S9. In this example, since "Action" of a record having "CRL" as the measured item in the cursor position determination table 61 is "ON", the process goes to Step S2.

Figure 6B:
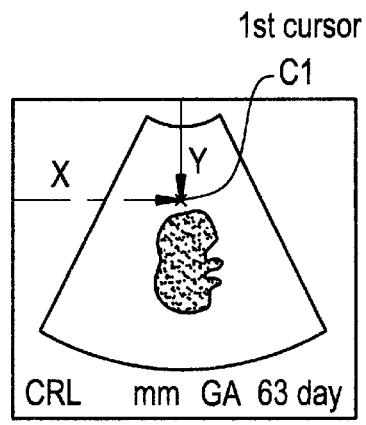

In Step S2, a first cursor C1 is initially displayed at the x-y coordinate which is specified in "First cursor position" of the record found in Step S1, as shown in FIG. 6(b). Since variance in the image position of the object (fetus F) is small, the first cursor C1 is initially displayed close to the image of the object (the head or the rump of the fetus F) if the cursor position determination table 61 is properly defined.

Figure 6C:
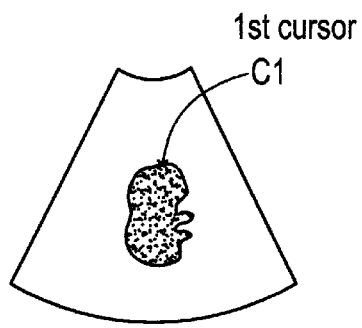

Then the operator moves the first cursor C1 and positions it at the image of the object as shown in FIG. 6(c). Since the first cursor C1 is initially displayed close to the image of the object as described above, the amount of operation required for the operator to move the first cursor C1 can be decreased.

In Step S3, the process waits for the position for the first cursor C1 to be determined, and when it is determined, the process goes to Step S4.

In Step S4, the value of "Second cursor position" of the record found in Step S1 is examined. If the value contains a function and its variable is not input, the process goes to Step S11, otherwise to Step S5. In this example, since "Second cursor position" of a record having "CRL" as the measured item in the cursor position determination table 61 contains the function (+f(GA)) and its variable GA has been input, the process goes to Step S5.

In Step S5, the initial position for the second cursor is obtained from the value of "Second cursor position" of the record found in Step 1. In this example, since the value of "Second cursor position" of a record having "CRL" as the measured item for the second cursor is found to be (+0, +function (+f(GA))) from the cursor position determination table 61, the x-coordinate of the initial position is set to the same value as the x-coordinate of the first cursor C1 and the y-coordinate of the initial position is set to a value equal to the value of the y-coordinate of the first cursor C1 plus 21 mm (=f(63)).

In Step S6, a check is made whether the initial position for the second cursor obtained in Step S5 is within the display region. If so, the process goes to Step S7, otherwise to Step S11.

Figure 6D:
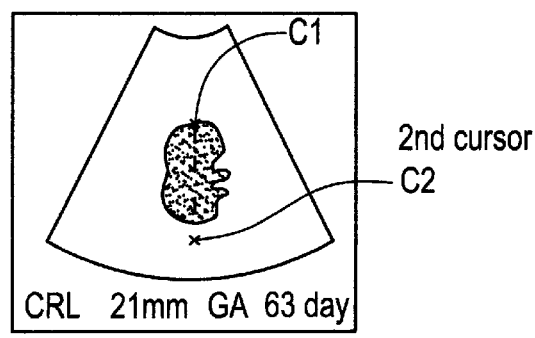

In Step S7, the second cursor C2 is displayed at its initial position obtained in Step S5, as shown in FIG. 6(d). In this example, since the initial position is obtained from the CRL value which normally corresponds to the GA estimated from the last menstruation date, the second cursor C2 is initially displayed close to the rump or the head of the fetus F. Since deviation of the initial display position of the second cursor C2 at that time from the rump or the head of the fetus F represents deviation of the CRL value of the fetus F from a normal value, i.e., represents growth, the operator may distinctly view excess or lack of growth.

In addition, the input GA value (estimated from the last menstruation date) and the CRL value which normally corresponds thereto are also displayed on the screen.

Figure 6E:
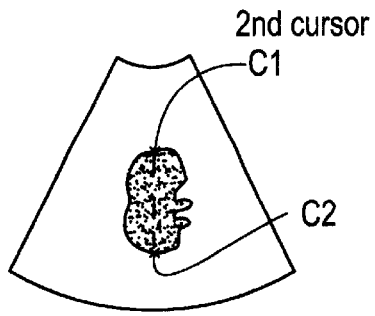

The operator moves the second cursor C2 and positions it at the image of the object, as shown in FIG. 6(e). Since the second cursor C2 is initially displayed close to the image of the object as described above, the amount of operation required for the operator to move the second cursor C2 can be decreased.

In Step S8, the process waits for the position for the second cursor C2 to be determined, and when it is determined, the cursor display processing routine is terminated and the process goes to the measuring routine which is not shown in the drawing.

Figure 6F:
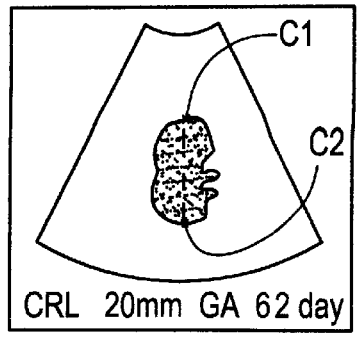

In the measuring routine, the CRL value and the GA value estimated therefrom are displayed on the screen as shown in FIG. 6(f).

In Step 9, the first cursor C1 is initially displayed in an initial position at the center of the screen.

Then the operator moves the first cursor C1 and positions it at the image of the object.

In Step S10, the process waits for the position for the first cursor C1 to be determined, and when it is determined, the process goes to Step S11.

In Step S11, the second cursor C2 is initially displayed in an initial position located 10 mm straight below the first cursor C1.

Then the operator moves the second cursor C2 and positions it at the image of the object.

Thereafter, the process returns to Step S8.

The above-described ultrasonic diagnostic apparatus 100 provides the following effects:

(1) The cursors C1 and C2 can be initially displayed at initial positions which are determined according to a measured item, and therefore the amount of operation required for moving the cursors C1 and C2 in positioning them at the image of the object can be decreased;

(2) The second cursor C2 is initially displayed at an initial position which is obtained based upon normal correlation with a known second attributive value, and therefore the amount of operation required for moving the second cursor C2 in positioning it at the image of the object can be decreased; and (3) Deviation of the initial display position of the second cursor C2 from the image of the object represents deviation of the first attributive value of the object from a normal value, thus allowing the operator to distinctly view deviation of the object from normal without using a graph.

In another embodiment, the initial position for the first cursor C1 may be fixed at the center of the screen. In this case, the cursor position determination table 61 can be simplified.

Although CRL of a fetus is taken as an example in the above description, the present invention can be applied to the ventricle area measurement for the heart and the like.

Many widely different embodiments of the invention may be configured without departing from the spirit and the scope of the present invention. It should be understood that the present invention is not limited to the specific embodiments described in the specification, except as defined in the appended claims.

I claim:

1. An ultrasonic diagnostic apparatus comprising:

image display means for displaying on a screen an image of an object taken by an ultrasonic probe;

first cursor initial display means for initially displaying a first cursor on the screen;

first cursor positioning means for moving the first cursor and positioning it in response to an operation by an operator;

second cursor initial display means which finds a normal value with respect to an on-screen positional relationship between the first cursor and a second cursor from normal correlation between first and second attributive values of the object, then finds an initial position for the second cursor based on the normal value and the position of the first cursor, and initially displays the second cursor at the initial position on the screen;

second cursor positioning means for moving the second cursor and positioning it in response to an operation by the operator; and measuring means for measuring the first attributive value of the object using an on-screen positional relationship between the first and second cursors.

2. The ultrasonic diagnostic apparatus of claim 1, the first cursor is initially displayed at an initial position according to the first attributive value, instead of at a fixed position.

3. The ultrasonic diagnostic apparatus of claim 1, wherein the object is a fetus, the first attributive value is CRL (Crown Rump Length), and the class of the second attributive value is GA (Gestation Age).

* * * * *